(12) United States Patent
Romano et al.

(10) Patent No.: US 6,333,150 B1
(45) Date of Patent: *Dec. 25, 2001

(54) ISOTHERMAL TRANSCRIPTION BASED ASSAY FOR THE DETECTION AND GENOTYPING OF DENGUE VIRUS

(75) Inventors: Joseph W. Romano, Derwood; Eun Mi Lee, Gaithersburg, both of MD (US); Gregory J. Hurteau, Alexandria, VA (US)

(73) Assignee: Akzo Nobel N.V. (NL)

(*) Notice: Subject to any disclaimer, the term of this patent is extended or adjusted under 35 U.S.C. 154(b) by 0 days.

This patent is subject to a terminal disclaimer.

(21) Appl. No.: 09/374,584

(22) Filed: Aug. 13, 1999

Related U.S. Application Data

(63) Continuation of application No. 09/002,177, filed on Dec. 31, 1977, now Pat. No. 5,968,732.

(51) Int. Cl.[7] .................. C12Q 1/70; C12Q 1/68; C07H 21/02; C07H 21/04; C12N 15/00
(52) U.S. Cl. ................. 435/5; 435/6; 536/23.1; 536/24.3; 935/76; 935/77; 935/78
(58) Field of Search .................. 435/6, 91.2; 536/23.1, 536/24.3; 935/76, 77, 78

(56) References Cited

U.S. PATENT DOCUMENTS

| | | |
|---|---|---|
| 5,234,809 | 8/1993 | Boom et al. . |
| 5,407,819 * | 4/1995 | Yahara et al. . |
| 5,409,818 | 4/1995 | Davey et al. . |
| 5,518,880 * | 5/1996 | Leonard et al. . |
| 5,554,517 | 9/1996 | Davey et al. . |
| 5,712,385 * | 1/1998 | McDonough et al. . |
| 5,721,118 * | 2/1998 | Scheffler . |
| 5,939,254 * | 8/1999 | Ennis et al. . |
| 5,968,732 * | 10/1999 | Romano et al. . |
| 5,968,734 * | 10/1999 | Aurias et al. . |
| 5,994,076 * | 11/1999 | Chenchik et al. . |
| 6,015,892 * | 1/2000 | Bennett et al. . |
| 6,017,535 * | 1/2000 | Fu et al. . |
| 6,074,865 * | 6/2000 | Kelly et al. . |
| 6,190,859 * | 2/2001 | Putnal et al. . |

FOREIGN PATENT DOCUMENTS

| | | |
|---|---|---|
| 2279652 | 1/1995 | (GB) . |
| WO 9306214 | 4/1993 | (WO) . |
| WO 9640933 | 6/1995 | (WO) . |
| WO 9640933 | 12/1996 | (WO) . |
| WO 9849351 | 11/1998 | (WO) . |

OTHER PUBLICATIONS

R. Rico–Hesse et al., *Virology*, 230:244–251, 1997.
E. Chungue et al., *Journal of Medical Virology*, 40:142–145, 1993.
R. Lanciotti et al., *Journal of Clinical Microbiology*, 30:3:545–551, 1992.
V. Vorndam et al., *Journal of Virological Methods*, 48:237–244, 1994.
E. Henchal et al., *Am. J. Trop. Med. Hyg.*, 45(4):418–428, 1991.
T.M. Sudhiro, *Am. J. Trop. Med. Hyg.*, 56(4):424–429, 1997.
Lewis et al., *Journal of Virological Methods*, 38:11–23, 1992.
Romano et al., *Clinics in Laboratory Medicine*, 16:1:89–103, 1996.
Morita et al., *Journal of Clinical Microbiology*, 29:10:2107–2110, 1991.
Killen et al., *Journal of Virological Methods*, 41:135–146, 1986.
Kerschner et al., *Journal of General Virology*, 67:2645–2661, 1986.
Wattre, Jan.–Feb. 1997, Annales De Biologi Clinique, vol. 55, (1), p. 25–31. (Abstract).

* cited by examiner

*Primary Examiner*—Ethan Whisenant
(74) *Attorney, Agent, or Firm*—Rothwell, Figg, Ernst & Manbeck, p.c.

(57) ABSTRACT

An isothermal transcription based amplification assay for dengue virus RNA uses primer combinations for sequences within the envelope gene or the 3' non-coding region of the virus and a probe. Probes may be specific for a serotype of dengue virus.

25 Claims, 3 Drawing Sheets

ISOTHERMAL TRANSCRIPTION BASED ASSAY FOR THE DETECTION AND GENOTYPING OF DENGUE VIRUS

This application is a Continuation of Ser. No. 09/002,177 filed Dec. 31, 1997 now U.S. Pat. No. 5,968,732.

FIELD OF THE INVENTION

The present invention is directed to an isothermal transcription based assay for the detection and genotyping of dengue virus. The present invention is also directed to oligonucleotides for amplifying dengue RNA and for type-specific probes used in the detection of the amplification product.

BACKGROUND OF THE INVENTION

Dengue virus infection is an arthropod-borne viral disease which has very high morbidity and mortality in humans. Dengue is a member of Flaviviridae, and utilizes an 11 kb single stranded, positive RNA genome. The genome encodes 3 proteins and contains additional non-coding regions at the 5' and 3' ends.

There are currently four different dengue virus subtypes known, which are distributed among geographically distinct tropical and subtropical regions. All four subtypes can cause an array of maladies, ranging from an acute, self limited illness (dengue fever, DF) to the more severe and potentially fatal dengue hemorrhagic fever or dengue shock syndrome (dengue hemorrhagic fever, DHF). As many as 50 million human cases occur annually, with an estimated 10,000 infant deaths due to the hemorrhagic form of dengue. Immunity to one serotype does not protect against infection by the others. In fact, sequential infection by another serotype substantially increases the probability of developing DHF (Rico-Hesse et al, Virology 230, 244–251 (1997)). For this reason it may be critical to be able to determine the genotype of the dengue virus for management of the disease.

Diagnosis and management of the disease, as well as vector surveillance and epidemiological studies, would be facilitated by a rapid and sensitive assay for the specific type of dengue involved. Extensive cross reactions among the flaviviruses and the existence of four distinct dengue virus serotypes makes serotype identification difficult. Currently, the most reliable method for identification involves isolation of the virus in a sensitive host followed by serotype identification using reference antisera or monoclonal antibodies. This method usually takes two or more weeks, however. Alternatively, a four-fold or greater increase in antibody titer by standard serological tests can be used, but generally requires paired samples. An ELISA for the detection of dengue virus-specific IgM in patient serum has also been used in diagnosis; however, this assay has been shown to be of very limited sensitivity.

As a consequence of the limitations of the above methods, several attempts have been made to devise RT-PCR based assays for the detection and genotyping of dengue virus infection (Henchal et al, Am. J. Trop. Med. Hyg., 45(4), 1991, pp. 418–428; Lanciotti et al, Journal of Clinical Microbiology, 30(3), March 1992, p. 545–551; Chungue et al, Journal of Medical Virology, 40:142–145,1993; Vorndam et al, Journal of Virological Methods, 48(1994) 237–244; and Sudiro et al, Am. J. Med. Hyg., 56(4), 1997, pp. 424–429). These assays have relied on alternative strategies, including universal or specific primer amplification and probe detection, differential nested amplification, and RFLP analysis of the PCR products. To date, isothermal amplification methods for dengue RNA have not been reported.

SUMMARY OF THE INVENTION

The present invention provides isothermal transcription based amplification assays for the detection and genotyping of dengue virus. The detection assay may use primer pairs and probes for the envelope gene of dengue virus type 2. In another embodiment of the invention, primer pairs and probes from the 3' non-coding region of the virus are used for the detection and genotyping of dengue virus.

Amplification in an isothermal transcription based amplification system is achieved through the coordinated activities of three enzyme activities (reverse transcriptase, RNase H, and RNA polymerase) and two DNA oligonucleotides (referred to herein as primers) specific for the target sequence. The method starts with an RNA template and alternately synthesizes DNA and RNA. Using an RNA template, a primer, and reverse transcriptase, an RNA/DNA hybrid is generated. The RNA is degraded from the hybrid by the RNase H activity. A double stranded DNA is then generated by the reverse transcriptase using another primer, and then the double stranded DNA is used as template for large amounts of RNA synthesis by the RNA polymerase. One of the primers has, in addition to the sequences complementary to the template, additional sequences necessary for generating an RNA polymerase promoter and transcription initiation site which can be used by the RNA polymerase. The single stranded RNA product can be readily detected through the hybridization of an appropriately labeled oligonucleotide DNA probe, with or without an additional probe which can be used to immobilize the amplification product. Detection of an amplification product indicates that the target molecule (RNA) is present in the sample.

DETAILED DESCRIPTION OF THE INVENTION

Figure 1:
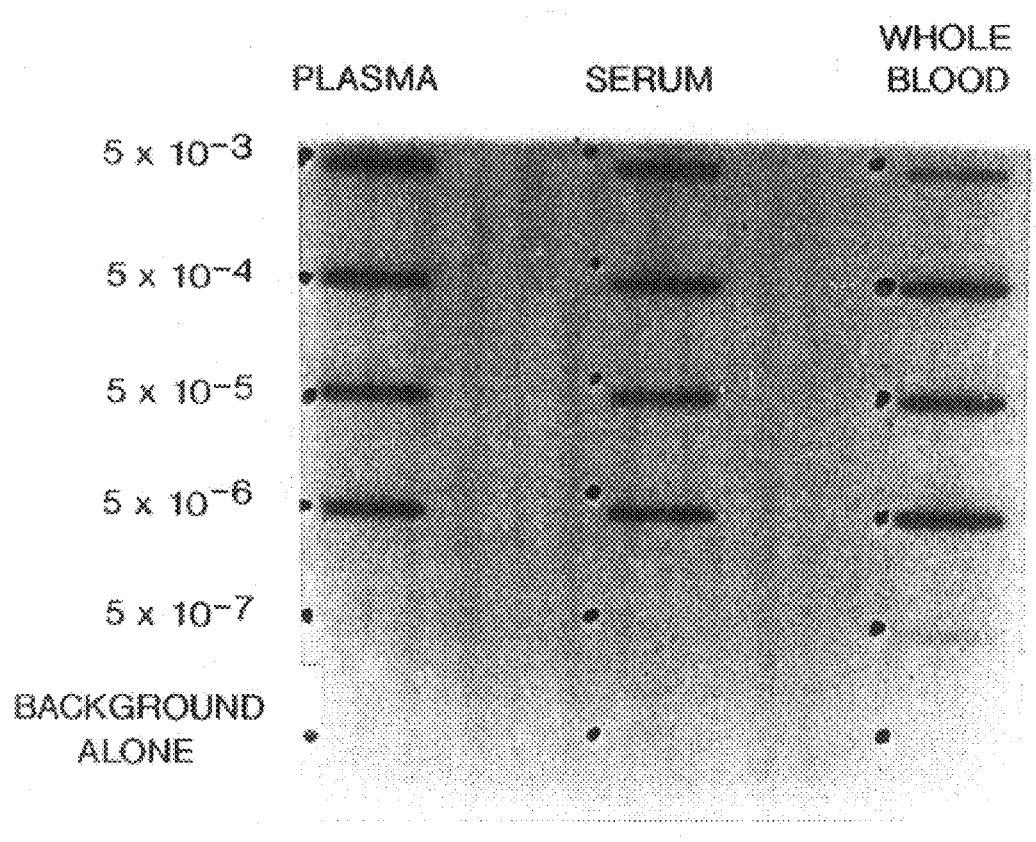
FIG. 1 is an autoradiogram of the products of an isothermal transcription based amplification assay of RNA extracts obtained from virus stocks spiked into blood, serum, and plasma background using primers in the envelope region with a probe as described in Example 2.
Figure 2:
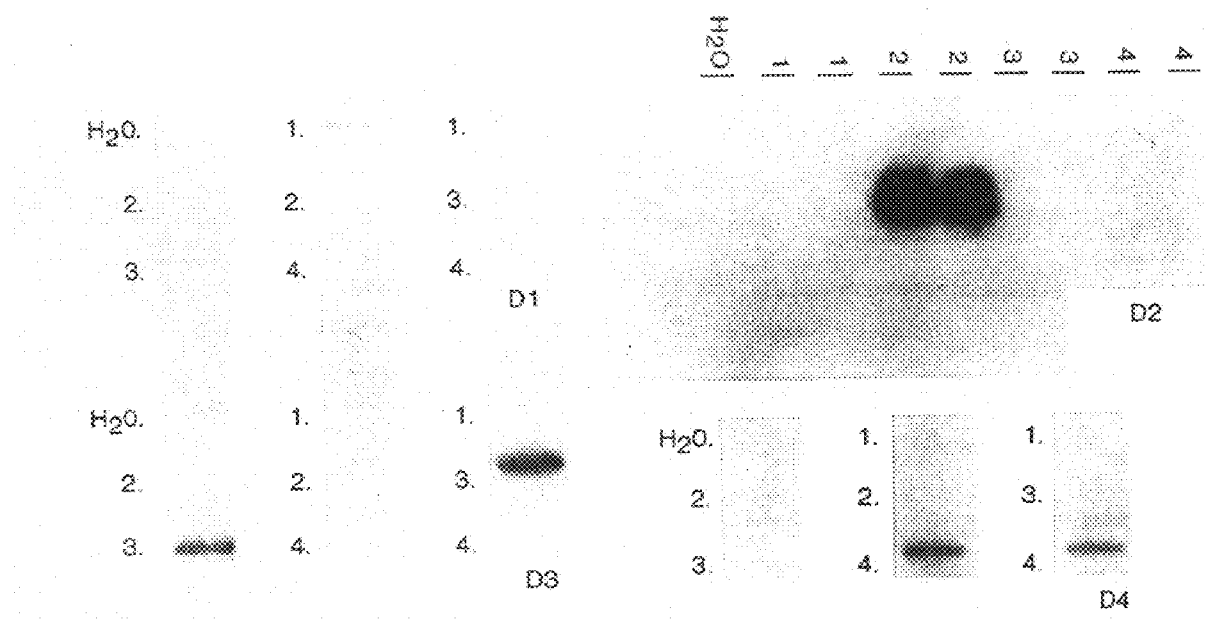
FIG. 2 is an autoradiogram of the products of an isothermal transcription based assay of RNA extracts obtained from virus stocks using primers in the 3' non-coding region with type specific probes as described in Example 3.

An isothermal transcription based assay is used for the detection and genotyping of dengue RNA. Any isothermal transcription based assay may be used with the primers and probes of the present invention. The isothermal transcription based assay of the present invention is carried out under conditions that can be readily determined by a person of ordinary skill in the art.

The preferred amplification method of the present invention is the isothermal transcription based amplification system referred to as NASBA. The NASBA method is disclosed in U.S. Pat. Nos. 5,409,818 and 5,554,527, which are herein incorporated by reference. NASBA includes the use of T7 RNA polymerase to transcribe multiple copies of RNA from a template including a T7 promoter.

Another technique for the amplification of nucleic acid is the so-called transcription based amplification system (TAS). The TAS method is described in International Patent Application No. WO 88/10315. Transcription based amplification techniques usually comprise treating target nucleic acid with two oligonucleotides one of which comprises a promoter sequence, to generate a template including a functional promoter. Multiple copies of RNA are transcribed from said template and can serve as a basis for further amplification.

Other transcription based amplification techniques are described in EP 408295. EP 408295 is primarily concerned with a two-enzyme transcription based amplification method. Transcription based amplification methods, such as the NASBA method described in EP 329822, are usually employed with a set of oligonucleotides, one of which is provided with a promoter sequence that is recognized by an enzyme with DNA dependent RNA polymerase activity such as, for example, T7 polymerase. Several modifications of transcription based techniques are known in the art. These modifications comprise, for example, the use of blocked oligonucleotides (that may be provided with a promoter sequence). These oligos are blocked so as to inhibit an extension reaction proceeding therefrom (U.S. Pat. No. 5,554,516). One or more "promoter-primers" (oligonucleotides provided with a promoter sequence) may be used in transcription based amplification techniques, optionally combined with the use of one or more oligonucleotides that are not provided with a promoter sequence.

The term "oligonucleotide" as used herein refers to a molecule comprised of two or more deoxyribonucleotides or ribonucleotides. Such oligonucleotides may be used as primers and probes.

Of course, based on the sequences of the oligonucleotides of the present invention, analogues of oligonucleotides can also be prepared. Such analogues may constitute alternative structures such as "PNA" (molecules with a peptide-like backbone instead of the phosphate sugar backbone of normal nucleic acid) or the like. It is evident that these alternative structures, representing the sequences if the present invention are likewise part of the present invention.

The term "primer" as used herein refers to an oligonucleotide either naturally occurring (e.g., as a restriction fragment) or produced synthetically, which is capable of acting as a point of initiation of synthesis of a primer extension product which is complementary to a nucleic acid strand (template or target sequence) when placed under suitable conditions (e.g., buffer, salt, temperature and pH) in the presence of nucleotides and an agent for nucleic acid polymerization, such as DNA dependent or RNA dependent polymerase. A primer must be sufficiently long to prime the synthesis of extension products in the presence of an agent for polymerization. A typical primer contains at least 10 nucleotides in length of a sequence substantially complementary or homologous to the target sequence, but somewhat longer primers are preferred. Usually primers contain about 15–26 nucleotides but longer primers may also be employed, especially when the primers contain additional sequences such as a promoter sequence for a particular polymerase.

Normally a set of primers will consist of at least two primers, one "upstream" (P2) and one "downstream" (P1) primer which together define the amplificate (the sequence that will be amplified using said primers). One of the primers is understood to contain, in addition to sequences that will hybridize to the target sequence, sequences which provide promoter activity. Most often the P1 primer will include the promoter sequence.

The term "promoter sequence" defines a region of a nucleic acid sequence that is specifically recognized by an RNA polymerase that binds to a recognized sequence and initiates the process of transcription by which an RNA transcript is produced. In principle, any promoter sequence may be employed for which there is a known and available polymerase that is capable of recognizing the initiation sequence. Known and useful promoters are those that are recognized by certain bacteriophage RNA polymerases such as bacteriophage T3, T7 or SP6. Their function as a primer, e.g., the starting point for an elongation reaction, however, may be blocked, as already mentioned above, or absent in some embodiments of transcription based amplification reactions. A particularly preferred promoter sequence is the sequence of the T7 RNA polymerase promoter. The preferred downstream primer sequences are shown below.
AATTCTAATACGACTCACTATAGGGAC-GAACCTTTTGTCCTGCTCTTCA (SEQ ID NO:18)
AATTCTAATACGACTCACTAT-AGGGGCAGCGAGAATCTGTTGTTGTGTT (SEQ ID NO:19)
AATTCTAATACGACTCACTATAGGGAAA-CACTCCTCCCAGGGATCCAAA (SEQ ID NO:20)
AATTCTAATACGACTCACTAT-AGGGCAGCCCCATAGATTGCTCCGAAAA (SEQ ID NO:21)
AATTCTAATACGACTCACTATAGGG-GAGACAGCAGGATCTCTGGTCT (SEQ ID NO:22)

SEQ ID NOs 18–22 comprise the sequences of SEQ ID NOs 1–2, 6–7, and 11 operably linked to the T7 promoter sequence, shown in italics. This makes the sequences especially suitable for use as downstream primer in a transcription based amplification technique such as NASBA.

A preferred embodiment of the present invention is a combination of two oligonucleotides according to the invention, for use as a set in nucleic acid amplification.

One of the oligonucleotides may serve as an "upstream oligonucleotide", i.e., upstream primer, while the second oligonucleotide serves as a "downstream oligonucleotide", i.e., downstream primer, in the amplification reaction.

Preferably, the reverse transcriptase activity is provided by avian myeloblastosis virus (AMV) reverse transcriptase and the RNA polymerase is provided by T7 RNA polymerase.

One of the advantages of an isothermal transcription based amplification method, as compared to other amplification methods such as PCR, is that by being essentially isothermal, it requires few manipulations by the experimenter. However, the absence of a high temperature step does make it somewhat more difficult to find appropriate primers (see below).

The amplification method of the present invention may be applied to extracts of samples comprising nucleic acid, or whole cells or tissues for in situ amplification. The samples may be various body fluids, particularly blood, plasma, and serum, from humans. The samples may also be tissue samples from humans. For use in epidemiological and surveillance studies, the samples may also be mosquito tissue, tissue culture media or cultured cells, or body fluids from non-human animals.

If the method is applied to extracts of samples comprising nucleic acids, the sample may be total RNA extracts (such as those described in Chomczynski and Sacchi, *Anal. Biochem.* 162:156, 1987) or "Boom" extracts (Boom et al, *J. Clin. Micro.*: 28, No. 3, March 1990, p. 495–503), which is herein incorporated by reference. The method is preferably applied to "Boom extracts".

The amplificate is detected by hybridization with an appropriately labeled A oligonucleotide probe. The label may contain a radioactive moiety, a detectable enzyme, or any other moiety capable of generating a detectable signal, such as a calorimetric, fluorescent, chemiluminescent or electrochemiluminescent (ECL) signal. Blot based hybridization analysis and liquid hybridization based ECL analysis are preferably used, although other analysis systems such as ELGA (enzyme-linked gel assay) and in situ hybridization can also be used.

In one embodiment of the present invention, the amplification products are resolved by agarose gel electrophoresis, then transferred to nylon membranes and hybridized to a probe that is 5'-end labeled with $^{32}P$ using standard methods. The products are then visualized by autoradiography. In a second embodiment of the present invention, the amplification products can be detected using the ELGA. In this method the products of the amplification reaction are resolved on a polyacrylamide gel. A probe that is specific for the amplification reaction product and conjugated at its 5' end with horseradish peroxidase (HRP) is then hybridized. A colorimetric enzyme reaction allows for the visualization of the reaction product in the gel. A third embodiment of the present invention makes use of electrochemiluminescence chemistry (or ECL). This embodiment uses a biotinylated capture probe immobilized onto the surface of a streptavidin-coated magnetic bead via the biotin-avidin interaction. This system also requires an oligonucleotide detector probe, which can hybridize to an independent region of the amplification product. This detector probe is labeled with Ruthenium, the substance that is responsible for generating an ECL signal.

The amplification methods of the invention may be used with one or more internal controls to monitor the efficiency of the extraction process and the amplification assay itself. The detection systems are described in detail in Romano et al, *DNA Technology* 16:89–103 (1996), and van Gemen et al., *J. of Virol. Methods*, 49:157–168 (1994), which are herein incorporated by reference. Methods for internal controls are described in van Gemen et al, *Reviews in Medical Virology*, 5:205–211 (1995), which is herein incorporated by reference.

If the method is to be practiced on fixed preparations for in situ analysis, the method is performed as follows. Samples may include various body fluids or tissue samples. Lymph tissue is a preferred tissue for in situ analysis. The cells are fixed and then permeabilized to optimize permeability of the cell membranes. The fixatives are those standardly used in the art for cell or tissue preparations, such as acetone and methanol, ethanol, formalin, formaldehyde, paraformaldehyde, or Permafix®, and the permeabilization is done by proteinases, such as proteinase K or pepsinogen. The cells are then washed to remove all reagents that might inhibit the transcription based reaction. Permeabilization is done to the point that the cells allow entry of all necessary amplification reaction components, yet retain the targets and amplification products within the cells. In addition, cosolvents such as glycerol or DMSO may be added to optimize the NASBA reaction.

Detection of amplification products may be by direct labelling (with, for instance, biotin or digoxigenin—UTP) or by in situ hybridization with labelled probe. The direct labelling method requires that conditions can be optimized to remove unincorporated label while maintaining the amplification products.

In a particularly preferred embodiment of the present invention, the isothermal transcription based amplification method is used in concert with a particular RNA extraction technique ("Boom extraction", Boom et al, *J. Clin. Micro.*: 28, No. 3, March 1990, p. 495–503), and ECL detection (electrochemiluminescence). The advantages of the system are those associated with an amplification based assay capable of providing sequence level data. Although some of these same advantages exist for the RT-PCR (i.e., increased sensitivity over ELISA, gene sequence specificity), there are advantages of NASBA for RNA over RT-PCR. These include isothermal amplification, incorporation of reverse transcription into the amplification, application to wider array of specimen types (via Boom extract), and the sensitivity and dynamic range of the ECL detection.

The isothermal amplification is of particular importance to applications of the assay in developing regions or under field assay conditions, two important considerations relevant to dengue epidemiology. In light of these considerations, a colorimetric detection system applied to a dried blood spot collection would be ideal for a field assay for dengue.

Boom extracts are purified preparations of DNA and RNA. The Boom method is based on the lysing and nuclease inactivating properties of the chaotropic agent guanidinium thiocyanate (GuSCN) together with the nucleic acid binding properties of silica particles or diatoms. By using size fractionated silica particles, nucleic acids, including covalently closed circular, relaxed circular, linear double-stranded DNA, single stranded DNA, tRNA, mRNA, and rRNA, can be purified from a sample in less than one hour and recovered in the original reaction vessel.

A small sample is pipetted into a reaction vessel containing a solid nucleic acid carrier and a GuSCN containing lysis buffer. Lysis of the cells occurs and the released nucleic acids bind to the carrier. The carrier-nucleic acid complexes can be separated by centrifugation. Several wash steps follow and the complexes are then dried. The nucleic acids are eluted in an aqueous low-salt buffer in the initial reaction vessel and used for the amplification reaction.

In a preferred embodiment of the present invention, amplification is achieved in a 20 μL reaction containing 5 μL of the nucleic acid extract material in 10 μL of premix [Tris (40 mM) pH8.5; $MgCl_2$ (12 mM); KCl (70 mM); DTT (5 mM); dNTPs (each) (1 mM); rATP, rUTP, rCTP (2 mM); rGTP (1.5 mM); ITP (0.5 mM); DMSO (15%); P1 and P2, (0.2 μM); Sorbitol (1.5 M)]. This is then added to 5 μL of enzyme mix [BSA (2.1 μg/NASBA); RNase H (0.08 unit/NASBA); T7 RNA Polymerase (32 units/NASBA); and AMV-RT (6.4 units/NASBA)]. (The enzyme mixture must not be vortexed). If the nucleic acid sample decreases (5 μl), then the water volume increases accordingly so that the total volume stays 15 μl when the nucleic acid is added.

The method can be carried out as follows.
1. Mix premix.
2. Add 10 μl of premix to 5 μl of nucleic acid in an Eppendorf tube.
3. Incubate at 65° C. for 5 minutes.
4. Transfer to 41° C. heat block, incubate for 5 minutes.
5. Add 5 μl of enzyme mix.
6. Mix without vortexing.
7. Incubate at 41° C. for 5 minutes.
8. If the tops of the tubes have condensation from the cooling, they may be spun.
9. Incubate at 41° C. for 90 minutes.
10. Spin down samples and store at −20° C.

In the method of the present invention NASBA primers were designed using the standard approach for the envelope gene of dengue virus type 2. A total of eight primers were designed and synthesized; there were two primer combinations for two different target sequences within the envelope gene. The primers and probes are listed on Table 1.

analysis indicated that all eight primer combinations were functional in NASBA amplification (data not shown).

TABLE 1

| | | |
|---|---|---|
| TARGET AREA A: | | |
| P1B: 5'ACGAACCTTTTGTCCTGCTCTTCA 3' | (249–272) | SEQ ID NO:1 |
| P1A: 5'GCAGCGAGAATCTGTTGTTGTGTT 3' | (199–222) | SEQ ID NO:2 |
| P2A: 5'TTTGTAGAAGGGGTTTCAGGAGGA 3' | (31–54) | SEQ ID NO:3 |
| P2B: 5'AACATGGAAGCTGTGTGACGACGA 3' | (77–100) | SEQ ID NO:4 |
| Probe A: 5'GAAACAGAAGCCAAACAACCTGCC 3' | (139–162) | SEQ ID NO:5 |
| TARGET AREA B: | | |
| P1C: 5'AAACACTCCTCCCAGGGATCCAAA 3' | (1264–1287) | SEQ ID NO:6 |
| P1D: 5'CAGCCCCATAGATTGCTCCGAAAA 3' | (1316–1339) | SEQ ID NO:7 |
| P2C: 5'AGAAGCAGAACCTCCATTCGGAGA 3' | (1101–1124) | SEQ ID NO:8 |
| P2D: 5'AGGAGTAGAGCCGGGACAATTGAA 3' | (1140–1163) | SEQ ID NO:9 |
| ProbeB: 5'ATTGAGACAACAATGAGGGGAGCG 3' | (1204–1227) | SEQ ID NO:10 |
| ProbeC: 5'GGTGACACAGCTTGGGATTTTGGA 3' | (1246–1269) | SEQ ID NO:23 |

An additional set of primers and probes was selected for the detection and genotyping of dengue. These oligonucleotides are derived from the 3' non-coding region of the dengue genome. The primers will amplify all four serotypes of dengue virus, the probes D1–D4 will specifically bind to each type of dengue virus, and the capture probe can be used as a capture probe in a genotyping reaction, or alternatively as a detection probe in a detection assay. These oligonucleotides are shown on Table 2.

TABLE 2

| | | |
|---|---|---|
| Primers | | |
| P1 | GAGACAGCAGGATCTCTGGTCT | SEQ ID NO:11 |
| P2 | GGTTAGAGGAGACCCCTCCC | SEQ ID NO:12 |
| PROBES | | |
| D1 (type 1) | GGGAAGCTGTATCCTGGTGGTAAGG | SEQ ID NO:13 |
| D2 (type 2) | ATGAAGCTGTAGTCTCACTGGAAGG | SEQ ID NO:14 |
| D3 (type 3) | AGGGAAGCTGTACCTCCTTGCAAAG | SEQ ID NO:15 |
| D4 (type 4) | GAGGAAGCTGTACTCCTGGTGGAAG | SEQ ID NO:16 |
| CAPTURE | AAACAGCATATTGACGCTGGG | SEQ ID NO:17 |

EXAMPLE 1

NASBA-Initial Evaluation

The NASBA primers of Table 1 were tested as follows. RNA was extracted by the Boom method from dengue virus type 2 (New Guinea) stock produced from an in vitro culture system. The primers were used in four different combinations per target site in standard NASBA reactions with 5 $\mu$L of 1× Boom extract.

Amplification was achieved in a 20 $\mu$L reaction containing 5 $\mu$L of the nucleic acid extract material in Tris (40 mM) pH8.5; $MgCl_2$ (12 mM); KCl (70 mM); DTT (5 mM); dNTPs (each) (1 mM); rATP, rUTP, rCTP (2 mM); rGTP (1.5 mM); ITP (0.5 mM); DMSO (15%); P1 and P2, (0.2 $\mu$M); Sorbitol (1.5 M); BSA (2.1 $\mu$g/NASBA); RNase H (0.08 unit/NASBA); T7 RNA Polymerase (32 units/NASBA); and AMV-RT (6.4 units/NASBA).

The NASBA products were detected using Southern Blot analysis and $^{32}$P-labeled versions of the probes. The initial

EXAMPLE 2

Because dengue infection causes viremia, and samples of blood may therefore be used as samples for the NASBA assay for dengue virus, it was desirable to know if the assay was reliable in the background of blood samples. Serial dilutions of the dengue virus stock material were spiked into normal human whole blood, serum, and plasma, extracted by the Boom method, and used in a NASBA assay with the envelope gene primers P1D and P2D. The amplification products were resolved on a slot blot and probed with the envelope gene probe C. Results demonstrated that it was possible to amplify as little as $10^{-6}$ $\mu$L of original dengue virus stock material in a whole blood or blood component background (see FIG. 1). Thus, initial model system evaluation of the NASBA-based dengue virus assay demonstrated the feasibility of the assay for application on the type of clinical samples which are most likely to be used in clinical practice.

EXAMPLE 3

Genotyping

The oligonucleotides shown on Table 2 from the 3' non-coding region of the dengue genome were used for the genotyping of virus stock material.

FIG. 2 shows the results of a NASBA assay of RNA samples prepared from virus stocks using primers P1 and P2 of Table 2, with probes D1, D2, D3, and D4. The upper left quadrant shows hybridization with the type 1 probe to the products of the NASBA reaction using the indicated virus strains. The upper right quadrant shows hybridization with the type 2 probe to the products of the NASBA reaction using the indicated virus strains. The lower left quadrant shows hybridization with the type 3 probe to the products of the NASBA reaction using the indicated virus strains. The lower right quadrant shows hybridization with the type 4 probe to the products of the NASBA reaction using the indicated virus strains. Thus, each of the probes reacts only with the appropriate samples using proper hybridization conditions.

EXAMPLE 4

The type specific probe D1 was also used to test NASBA reaction products from clinical samples. Ten specimens which were previously identified as dengue type 1 by viral isolation and IFA were also tested by the method of the present invention.

Figure 3:
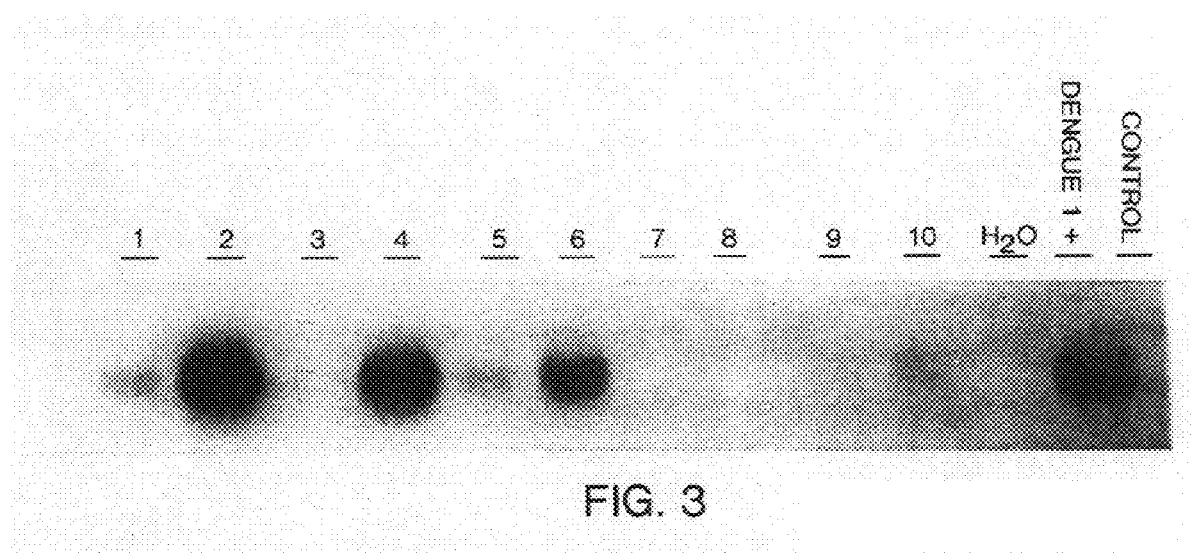
FIG. 3 is an autoradiogram of the products of an isothermal transcription based assay using primers in the 3' non-coding region of human plasma samples probed with a dengue type 1 probe as described in Example 4.

The samples were from patients diagnosed with dengue type 1. Cell cultures were inoculated with six of the samples and two of the six showed plaque formation. Five of the samples were tested by reverse transcriptase-PCR (RT/PCR) and none of the samples tested were positive in this assay. These 10 samples were then tested by the method of the present invention using the Boom extraction method, the NASBA amplification method and detection with radioactively labeled probe. Seven of the 10 were positive when probed with dengue type 1 probe, including three which were previously found to be negative in the RT/PCR assay. Samples 1, 5, 9, and 10 were considered positive, and samples 2, 4, and 6 were considered strongly positive (See FIG. 3). The amplification products were also tested with the dengue type 2 probe and all were negative (data not shown). The results are shown in TABLE 3.

TABLE 3

| SAMPLE | SEROTYPE (IFA) | PLAQUE ASSAY (PFU/ml) | RT/PCR | NASBA |
|---|---|---|---|---|
| 1 | 1 | $2 \times 10^5$ | – | + |
| 2 | 1 | 0 | – | ++ |
| 3 | 1 | 0 | – | – |
| 4 | 1 | ND | ND | ++ |
| 5 | 1 | ND | ND | + |
| 6 | 1 | ND | ND | ++ |
| 7 | 1 | ND | ND | – |
| 8 | 1 | 0 | – | – |
| 9 | 1 | 0 | – | + |
| 10 | 1 | 25 | ND | + |

ND = not done
+ = positive
++ = strongly positive

These results show that the amplification assay of the present invention is extremely sensitive in the detection of dengue virus RNA in clinical samples.

The biggest problem encountered in the development of NASBA assays is the selection of primers. It has often been the case that primers which are selected from sequence data, and meet all the known requirements for primers, do not actually function in practice. In addition, in some cases primers have been developed using model systems Sush as in vitro transcribed RNA, virus stocks, or cells lines with very high expression of the target gene, but those primers were found to be nonfunctional when the target molecule is in a background of clinical samples. The exact mechanism underlying this problem is not understood, but is believed to arise due to the lower temperature of the NASBA reaction, which does not entirely melt secondary structure of the target molecule and may permit nonspecific annealing of primer to background nucleic acids in the sample. It is essential for the application of the NASBA system to clinical samples that the primers be not absorbed by background nucleic acids, but rather be available for specific binding to the target molecule.

The results shown in the present application demonstrate that the primers and probes of the present invention can specifically detect low levels of target molecule, even in the background of clinical samples. Thus, the primers used in the present invention provide unexpectedly good results for the detection and genotyping of dengue virus.

We claim:

1. A method for the detection of dengue virus RNA, comprising:
    a) obtaining a sample which may contain dengue virus RNA;
    b) performing an isothermal transcription based amplification on the sample with two oligonucleotide primers, a first primer which comprises at least 10 consecutive nucleotides of a sequence selected from the group consisting of SEQ ID NO:1, SEQ ID NO:2, SEQ ID NO:6 and SEQ ID NO:7, and a second primer which comprises at least 10 consecutive nucleotides of a sequence selected from the group consisting of SEQ ID NO:3, SEQ ID NO:4, SEQ ID NO:8 and SEQ ID NO:9; and
    c) detecting the amplification product using a labeled probe, whereby hybridization of the probe to the amplification product indicates the presence of dengue virus RNA in the sample.

2. The method of claim 1, wherein the first primer further comprises an RNA polymerase promotor sequence covalently bonded to the 5' end thereof.

3. The method of claim 2, wherein the RNA polymerase promoter sequence is a T7 RNA polymerase promoter sequence.

4. The method of claim 1, wherein the sample comprises cells or virus and RNA is extracted from the cells or virus in the sample prior to step (b).

5. The method of claim 1, wherein the probe is selected from the group consisting of SEQ ID NO:5 and SEQ ID NO:10.

6. A method for the detection or genotyping of dengue virus RNA in a sample comprising:
    a) obtaining a sample which may contain dengue virus RNA;
    b) performing an isothermal transcription based amplification on the sample with two primers, a first primer which comprises at least 10 consecutive nucleotides of a sequence according to SEQ ID NO:11, and a second primer which comprises at least 10 consecutive nucleotides of a sequence according to SEQ ID NO:12; and
    c) detecting or genotyping the amplification product using one or more probes.

7. The method of claim 6, wherein the first primer further comprises an RNA polymerase promoter sequence covalently bonded to the 5' end thereof.

8. The method of claim 7, wherein the RNA polymerase promoter sequence is a T7 RNA polymerase promoter sequence.

9. The method of claim 6, wherein the sample comprises cells or virus and RNA is extracted from the cells or virus in the sample prior to step (b).

10. The method of claim 6, wherein the probe is selected from the group consisting or SEQ ID NO:13, SEQ ID NO:14, SEQ ID NO:15, SEQ ID NO:16 and SEQ ID NO:17, whereby hybridization of the amplification product with SEQ ID NO:13 indicates the virus RNA is type 1, hybridization of the amplification product with SEQ ID NO:14 indicates the virus RNA is type 2, hybridization of the amplification product with SEQ ID NO:15 indicates the virus RNA is type 3, hybridization of the amplification product with SEQ ID NO:16 indicates the virus RNA is type 4, and wherein hybridization of the amplification product with SEQ ID NO:17 indicates the presence of dengue virus RNA.

11. A kit for the detection or genotyping of dengue virus RNA in a sample, comprising two oligonucleotide primers, a first primer being about 15–26 nucleotides in length and comprising at least 10 consecutive nucleotides of a sequence according to SEQ ID NO:11, and a second primer being about 15–26 nucleotides in length and comprising at least 10 consectutive nucleotides of a sequence according to SEQ ID NO:12, and at least one probe.

12. A kit according to claim 11, wherein the at least one probe is selected from the group consisting of SEQ ID NO:13, SEQ ID NO:14, SEQ ID NO:15, SEQ ID NO:16 and SEQ ID NO:17.

13. A kit for the detection of dengue virus type 2 RNA in a sample, said kit comprising two oligonucleotide primers, a first primer being about 15–26 nucleotides in length and comprising at least 10 consecutive nucleotides of a sequence selected from the group consisting of SEQ ID NO:1, SEQ ID NO:2, SEQ ID NO:6 and SEQ ID NO:7, and a second primer being about 15–26 nucleotides in length and comprising at least 10 consecutive nucleotides of a sequence selected from the group consisting of SEQ ID NO:3, SEQ ID NO:4, SEQ ID NO:8, and SEQ ID NO:9; and a probe.

14. A kit according to claim 13, wherein the probe is selected from the group consisting of SEQ ID NO:5, SEQ ID NO:10, and SEQ ID NO:23.

15. An oligonucleotide of about 15–26 nucleotides in length comprising at least 10 consecutive nucleotides of a sequence selected from the group consisting of SEQ ID NO:1, SEQ ID NO:4, SEQ ID NO:5, SEQ ID NO:6, SEQ ID NO:9, SEQ ID NO:10, and SEQ ID NO:23.

16. The oligonucleotide of claim 15, comprising at least 10 consecutive nucleotides of a sequence selected from the group consisting of SEQ ID NO:1, SEQ ID NO:4 and SEQ ID NO:6, and SEQ ID NO:9.

17. The oligonucleotide of claim 15, comprising at least 10 consecutive nucleotides of a sequence selected from SEQ ID NO:1 and SEQ ID NO:6, further comprising an RNA polymerase promoter sequence covalently bonded to the 5' end thereof.

18. The oligonucleotide of claim 17, wherein the RNA polymerase promoter sequence is the T7 RNA polymerase promoter sequence.

19. An oligonucleotide of about 15–26 nucleotides in length, comprising at least 10 consecutive nucleotides of a sequence selected from the group consisting of SEQ ID NO:11, SEQ ID NO:12, and SEQ ID NO:14.

20. The oligonucleotide of claim 19, comprising at least 10 consecutive nucleotides of a sequence according to SEQ ID NO:11 or SEQ ID NO:12.

21. The oligonucleotide of claim 19, comprising at least 10 consecutive nucleotides of a sequence according to SEQ ID NO:11, further comprising an RNA polymerase promoter sequences covalently bonded to the 5' end thereof.

22. The oligonucleotide of claim 21, wherein the RNA polymerase promoter sequence is the T7 RNA polymerase promoter sequence.

23. The oligonucleotide of claim 22, wherein the oligonucleotide is a sequence according to SEQ ID NO:22.

24. An oligonucleotide of 15–26 nucleotides in length which is a subsequence of Dengue virus and which comprises at least 15 consecutive nucleotides of a sequence selected from the group consisting of SEQ ID NO:2, SEQ ID NO:3, SEQ ID NO:7, and SEQ ID NO:8, wherein said consecutive nucleotides are identical throughout their length to a Dengue virus genome.

25. An oligonucleotide of 15–26 nucleotides in length which is a subsequence of Dengue virus and which comprises at least 15 consecutive nucleotides of a sequence selected from the group consisting of SEQ ID NO:13, SEQ ID NO:15, SEQ ID NO:16, and SEQ ID NO:17, wherein said consecutive nucleotides are identical throughout their length to a Dengue virus genome.

* * * * *

SEQUENCE LISTING

<160> NUMBER OF SEQ ID NOS: 23

<210> SEQ ID NO 1
<211> LENGTH: 24
<212> TYPE: DNA
<213> ORGANISM: Dengue virus

<400> SEQUENCE: 1
acgaaccttt tgtcctgctc ttca                                        24

<210> SEQ ID NO 2
<211> LENGTH: 24
<212> TYPE: DNA
<213> ORGANISM: Dengue virus

<400> SEQUENCE: 2
gcagcgagaa tctgttgttg tgtt                                        24

<210> SEQ ID NO 3
<211> LENGTH: 24
<212> TYPE: DNA
<213> ORGANISM: Dengue virus

<400> SEQUENCE: 3
tttgtagaag gggtttcagg agga                                        24

<210> SEQ ID NO 4
<211> LENGTH: 24
<212> TYPE: DNA
<213> ORGANISM: Dengue virus

<400> SEQUENCE: 4
aacatggaag ctgtgtgacg acga 24

<210> SEQ ID NO 5
<211> LENGTH: 24
<212> TYPE: DNA
<213> ORGANISM: Dengue virus

<400> SEQUENCE: 5
gaaacagaag ccaaacaacc tgcc 24

<210> SEQ ID NO 6
<211> LENGTH: 24
<212> TYPE: DNA
<213> ORGANISM: Dengue virus

<400> SEQUENCE: 6
aaacactcct cccagggatc caaa 24

<210> SEQ ID NO 7
<211> LENGTH: 24
<212> TYPE: DNA
<213> ORGANISM: Dengue virus

<400> SEQUENCE: 7
cagccccata gattgctccg aaaa 24

<210> SEQ ID NO 8
<211> LENGTH: 24
<212> TYPE: DNA
<213> ORGANISM: Dengue virus

<400> SEQUENCE: 8
agaagcagaa cctccattcg gaga 24

<210> SEQ ID NO 9
<211> LENGTH: 24
<212> TYPE: DNA
<213> ORGANISM: Dengue virus

<400> SEQUENCE: 9
aggagtagag ccgggacaat tgaa 24

<210> SEQ ID NO 10
<211> LENGTH: 24
<212> TYPE: DNA
<213> ORGANISM: Dengue virus

<400> SEQUENCE: 10
attgagacaa caatgagggg agcg 24

<210> SEQ ID NO 11
<211> LENGTH: 22
<212> TYPE: DNA
<213> ORGANISM: Dengue virus

<400> SEQUENCE: 11

-continued

```
gagacagcag gatctctggt ct                                                  22

<210> SEQ ID NO 12
<211> LENGTH: 20
<212> TYPE: DNA
<213> ORGANISM: Dengue virus

<400> SEQUENCE: 12
ggttagagga gacccctccc                                                     20

<210> SEQ ID NO 13
<211> LENGTH: 25
<212> TYPE: DNA
<213> ORGANISM: Dengue virus

<400> SEQUENCE: 13
gggaagctgt atcctggtgg taagg                                               25

<210> SEQ ID NO 14
<211> LENGTH: 25
<212> TYPE: DNA
<213> ORGANISM: Dengue virus

<400> SEQUENCE: 14
atgaagctgt agtctcactg gaagg                                               25

<210> SEQ ID NO 15
<211> LENGTH: 25
<212> TYPE: DNA
<213> ORGANISM: Dengue virus

<400> SEQUENCE: 15
agggaagctg tacctccttg caaag                                               25

<210> SEQ ID NO 16
<211> LENGTH: 25
<212> TYPE: DNA
<213> ORGANISM: Dengue virus

<400> SEQUENCE: 16
gaggaagctg tactcctggt ggaag                                               25

<210> SEQ ID NO 17
<211> LENGTH: 21
<212> TYPE: DNA
<213> ORGANISM: Dengue virus

<400> SEQUENCE: 17
aaacagcata ttgacgctgg g                                                   21

<210> SEQ ID NO 18
<211> LENGTH: 49
<212> TYPE: DNA
<213> ORGANISM: Dengue virus

<400> SEQUENCE: 18
aattctaata cgactcacta tagggacgaa cctttgtcc tgctcttca                      49

<210> SEQ ID NO 19
<211> LENGTH: 49
<212> TYPE: DNA
<213> ORGANISM: Dengue virus

<400> SEQUENCE: 19
```

```
aattctaata cgactcacta tagggcagc gagaatctgt tgttgtgtt              49

<210> SEQ ID NO 20
<211> LENGTH: 49
<212> TYPE: DNA
<213> ORGANISM: Dengue virus

<400> SEQUENCE: 20
aattctaata cgactcacta tagggaaaca ctcctcccag ggatccaaa              49

<210> SEQ ID NO 21
<211> LENGTH: 49
<212> TYPE: DNA
<213> ORGANISM: Dengue virus

<400> SEQUENCE: 21
aattctaata cgactcacta tagggcagcc ccatagattg ctccgaaaa              49

<210> SEQ ID NO 22
<211> LENGTH: 47
<212> TYPE: DNA
<213> ORGANISM: Dengue virus

<400> SEQUENCE: 22
aattctaata cgactcacta tagggagac agcaggatct ctggtct                 47

<210> SEQ ID NO 23
<211> LENGTH: 24
<212> TYPE: DNA
<213> ORGANISM: Dengue virus

<400> SEQUENCE: 23
ggtgacacag cttgggattt tgga                                         24
```